United States Patent [19]

Marchbanks

[11] Patent Number: 5,767,126
[45] Date of Patent: Jun. 16, 1998

[54] ALZHEIMER'S DISEASE TREATMENT WITH TACRINE METABOLITES

[76] Inventor: Roger Michael Marchbanks, 26 Elms Rd., London, England, SW4 9EX

[21] Appl. No.: 142,342

[22] PCT Filed: May 7, 1992

[86] PCT No.: PCT/GB92/00828

§ 371 Date: Oct. 18, 1994

§ 102(e) Date: Oct. 18, 1994

[87] PCT Pub. No.: WO92/22534

PCT Pub. Date: Dec. 23, 1992

[30] Foreign Application Priority Data

Jun. 18, 1991 [GB] United Kingdom ............ 9113110
Mar. 7, 1992 [GB] United Kingdom ............ 9205019

[51] Int. Cl.⁶ .......................... A61K 31/435; C07D 219/10
[52] U.S. Cl. ............................................. 514/297; 546/105
[58] Field of Search ............................. 546/105; 514/297

[56] References Cited

U.S. PATENT DOCUMENTS 4,985,430  1/1991  Morita ........................... 514/253

FOREIGN PATENT DOCUMENTS 369388  5/1990  European Pat. Off. .

*Primary Examiner*—C. Warren Ivy
*Assistant Examiner*—Evelyn Huang

[57] ABSTRACT

Polyhydroxylated and dehydrogenated metabolites of 9-amino-1,2,3,4-tetrahydro-acridine (Tacrine) in which attached to at least two of the carbon atoms numbered 1,2,3 and 4 is a hydroxyl group and to the others either hydrogen, hydroxyl or double bonded oxygen the residual valencies being occupied by hydrogen or double bonds between carbon atoms 1 and 2 and/or 3 and 4 are disclosed as being useful medicaments for enhancing memory and cognitive function in Alzheimer's disease because they have retained the anticholinesterase activity of their metabolic precursor while circumventing its hepatotoxicity. Related compounds to which this disclosure also applies include those in which the aromatic ring is substituted with lower alkyl, lower alkoxy, halogen, hydroxy, nitro, trifluoromethyl, alkyl-N-substituted carboxamides and where the 9-amino group is mono or di-substituted independently. This disclosure also applies to stereo, optical and geometrical isomers of the above compounds and their pharmaceutically acceptable acid addition salts.

3 Claims, No Drawings

ALZHEIMER'S DISEASE TREATMENT WITH TACRINE METABOLITES

This application is the national phase of PCT/GB92/00828, filed on May 7, 1992, issued as WO92/22534 on Dec. 23, 1992.

DESCRIPTION

This invention relates to a method for treating Alzheimer's disease and similar cholinergic dysfunctions with polyhydroxylated and dehydrogenated derivatives of the compound 9-amino-1,2,3,4-tetrahydroacridine (Tacrine). Alzheimer's disease is a progressive deterioration of the brain resulting in loss of memory, cognitive deficits and depression. The illness has affected approximately 10% of the population by age 65 and its incidence increases by about 1% per year of the general population surviving from then. It is recognised as a major health care problem. The deterioration of the brain is known to cause a partial loss of the substance acetylcholine. The presence of this substance is essential for the proper functioning of memory so that certain drugs that cause its conservation will be of therapeutic benefit for Alzheimer's disease. Acetylcholine is destroyed in the brain by an enzyme known as acetylcholinesterase. The class of drugs that can prevent the action of this enzyme will cause the conservation of acetylcholine and thus are potentially able to restore the loss of memory.

Tacrine has been shown to prevent the action of acetylcholinesterase (P. N. Kaul, J. Pharm. Pharmacol. (1962), Vol 14, pages 237-242) and several studies most notably that by S. A. Eagger, R. Levy and B. J. Sahakian (Lancet (1991), Vol 337, pages 989-992) have demonstrated the effectiveness of Tacrine in restoring memory function in Alzheimer's disease. When Tacrine is withdrawn from the patient a relapse in cognitive function occurs so that continued administration would be necessary for effective therapy.

Unfortunately, as P. Hammell, D. Laney, J. Berman and others have shown Tacrine causes liver damage so that its prolonged use as a therapeutic agent is not possible (J. Clin. Gastroenterol (1990), Vol 12, pages 329-331).

According to the present invention certain compounds which result from the metabolism of Tacrine will not be toxic to the liver because it is their production in the liver itself which causes the damage to it. It is shown that such compounds retain their capacity to prevent the action of acetylcholinesterase provided that the carbon skeleton of the hydrogenated ring is not completely disrupted by metabolism. It is disclosed that the metabolism of Tacrine proceeds by dehydrogenation and hydroxylkation of the hydrogenated ring. It is also disclosed that polyhydroxylated and dehydrogenated derivatives retain their ability to prevent the action of acetylcholinesterase provided the carbon skeleton of the originally hydrogenated ring is not lost. The administration of such compounds will be of therapeutic benefit in the treatment of Alzheimer's disease because the hepatotoxic stages of the metabolism of Tacrine has been circumvented but the anticholinesterase activity conserved.

Embodiments of this invention will now be described with reference to the accompanying figure.

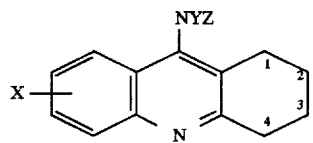

FIGURE Generic structure of metabolites of Tacrine. (In Tacrine itself X,Y, and Z all=hydrogen which is also the only and saturating substituent of carbon atoms numbered 1,2,3 & 4).

In this invention attached to at least two of the carbon atoms numbered 1,2,3 and 4 is a hydroxyl group and to the others either hydrogen, hydroxyl or double bonded oxygen, the residual valencies being occupied by hydrogen or double bonds between carbon atoms 1 and 2 and/or 3 and 4.

X is hydrogen, lower alkyl, lower alkoxy, halogen, hydroxy, nitro, trifluoromethyl, NHCOR where R is lower alkyl, or NR' R' where R' is independently hydrogen or lower alkyl. Y is hydrogen or lower alkyl. Z is hydrogen, lower alkyl, diloweralkylaminoloweralkyl, arylloweralkyl, furylloweralkyl, thienylloweralkyl.

Throughout this specification and appended claims a given chemical formula or name shall encompass all stereo and optical isomers as exist as well as pharmaceutically acceptable acid addition salts and solvates which are useful in the formulation of a pharmaceutical composition comprising an amount of the compound sufficient to improve cognitive function.

The following definitions shall apply throughout this specification and the appended claims.

The term lower alkyl denotes a straight or branched alkyl group having 1 to 6 carbon atoms. Examples of said lower alkyl include methyl, ethyl, n-propyl, iso-propyl, n-butyl, iso-butyl, sec-butyl, t-butyl and straight and branched chain pentyl and hexyl. A similar definition shall apply to the term lower alkoxy. The term halogen shall mean fluorine, chlorine, bromine or iodine. The term aryl shall mean an unsubstituted phenyl group or a phenyl group substituted with up to four groups each of which may be independently lower alkyl, lower alkoxy, halogen, hydroxy or trifluoromethyl.

The compounds of the present invention may be synthesised by a method deriving from that described in Tetrahedron letters (1963) page 1277 by Moore and Kornreich. Generally an aryl 1,2 amino-nitrile or amide substituted anthranilamide with ring substituents as required is condensed with a cyclohexanone derivative having hydroxyl groups or ketone functions as required on the carbon atoms except leaving one carbon atom adjacent to the carbonyl function unsubstituted. The condensation can be carried out at 40–120 degrees centigrade in a suitable solvent such as dioxane in the presence of zinc chloride for 1–4 hours. Following this the reaction mixture is treated with alkali at 20 degrees centigrade for 4–12 hours and the bases extracted into a suitable organic solvent. Purification can be carried out by recrystallisation of the hydrochloride or other acid addition salts followed by chromatography.

The compounds of the present invention as described above are useful in the treatment of cognitive dysfunction of Alzheimer's disease without the attendant liver toxicity of Tacrine. This utility is manifested by their ability to inhibit the enzyme acetylcholinesterase and thereby remedy cholinergic impoverishment by raising acetylcholine concentrations in the brain.

The acetylcholinesterase inhibition of some specific examples was determined by the photometric method of Ellman and others Biochem. Pharmacol. (1961), vol 7, pages 88–93.). pI values indicate by their magnitude the effectiveness in logarithmic terms of the compounds capacity to prevent the action of acetylcholinesterase. The figure for 4-aminoquinoline is obtained from the study by P. N. Kaul (op.cit) and is given to illustrate the ineffectiveness by about a thousand-fold of compounds that have lost the hydrogenated ring by metabolism.

| Compound | Cholinesterase inhibition pI |
|---|---|
| 9-amino-1,2,3,4-tetrahydroacridin-1,2-diol | 5.9 |
| 9-amino-1,2-dihydroacridin-1,2-diol | 6.2 |
| 9-amino-1,2,3,4-tetrahydroacridin-3,4-diol | 6.7 |
| 9-amino-1,2-dihydroacridin-1,2-diol 4(3H)-one | 6.3 |
| 9-amino-1,4-dihydroxyacridine | 6.5 |
| 9-amino-2,4-dihydroxyacridine | 6.8 |
| 9-amino-1,2,3,4-tetrahydroacridin-2,3,4-triol | 6.9 |
| 9-amino-1,2,3,4-tetrahydroacridin 1,2,3,4-tetraol | 6.8 |
| prior art compounds: | |
| 9-amino-1,2,3,4-tetrahydroacridine (Tacrine) | 7.9 |
| 4-aminoquinoline | 4.3 |

Effective quantities of the compounds of the invention may be administered to the patient by any of the following methods, for example orally, in capsules, tablets, parenterally in the form of suspensions or intravenously in the form of sterile solutions. The dosage units will be in the range 1–300 milligrams of active compound. Free base compounds may be administered of themselves or in combination with pharmaceutically acceptable acids such as hydrochloric, hydrobromic, sulphuric, phosphoric, perchloric and such organic acids as tartaric, citric or maleic.

Oral administration may be in the presence of an inert diluent or edible carrier. The compounds may be incorporated with excipients and used in the form of syrups, wafers etc. These preparations should contain between 1–300 milligrams of the active compound thus constituting about 0.5–50% of the total weight of the formulation. Glidants such as colloidal silica, disintegrants such as Primogel, alginic acid or cornstarch, lubricants such as magnesium stearate or Sterotex, binders such as gum tragacanth, gelatin or cellulose, excipients such as starch or lactose, sweeteners such as sucrose or saccharin or flavouring agents such as peppermint or orange may be added as appropriate to tablets or syrups. Capsules may contain a fatty oil as liquid carrier and may be coated with sugar or shellac. Solutions or suspensions to be parenterally administered may include sterile diluents such as water, saline, polyethylene glycols, glycerine, fixed oils, antibacterial agents, antioxidants, chelating agents, buffers and agents for the adjustment of tonicity the whole being enclosed in disposable syringes or multiple dose vials.

I claim:

1. A compound as shown wherein attached to at least two of the carbon atoms numbered 1,2,3 and 4 is a hydroxyl group and to the others either hydrogen, hydroxyl or double bonded oxygen, the residual valencies on carbon atoms numbered 1,2,3 and 4 being occupied by hydrogen or by double bonds between carbon atoms 1 and 2 and/or 3 and 4; X is hydrogen, lower alkyl, lower alkoxy, halogen, hydroxy, nitro, trifluoromethyl, NHCOR where R is lower alkyl, or NR' R' where R' is independently hydrogen or lower alkyl, Y is hydrogen or lower alkyl, Z is hydrogen, lower alkyl, arylloweralkyl, diloweralkylaminoloweralkyl, furylloweralkyl, thienylloweralkyl, stereo, optical and geometrical isomers thereof or its pharmaceutically acceptable acid addition salts.

2. A pharmaceutical composition useful for treating memory dysfunction related to Alzheimer's disease comprising of an effective amount of a compound as defined in claim 1 as active ingredient in association with a pharmaceutically acceptable carrier and/or adjuvant.

3. The method of treating memory dysfunction related to Alzheimer's disease without risk of hepatotoxicity in a patient in need of such treatment which comprises administering to such a patient an effective amount of the compound of claim 1.

* * * * *